United States Patent [19]

Sigl

[11] 4,300,967
[45] Nov. 17, 1981

[54] METHODS AND APPARATUS FOR ELASTICIZING DISCRETE AREAS OF CONFORMABLE GARMENTS

[75] Inventor: Wayne C. Sigl, Black Creek, Wis.

[73] Assignee: Kimberly-Clark Corporation, Neenah, Wis.

[21] Appl. No.: 94,421

[22] Filed: Nov. 15, 1979

[51] Int. Cl.³ .................. A61F 13/16; B32B 31/08; B32B 31/18; B65H 23/08
[52] U.S. Cl. ................... 156/164; 156/229; 156/269; 156/301; 156/322; 156/324; 156/495; 156/499; 156/516; 156/549; 156/554; 156/578
[58] Field of Search ............... 156/164, 229, 269, 300, 156/301, 322, 324, 494, 495, 499, 516, 549, 554, 578; 128/287, 290 R

[56] References Cited

U.S. PATENT DOCUMENTS

| | | | |
|---|---|---|---|
| 3,600,250 | 8/1971 | Evans | 156/322 |
| 3,828,367 | 8/1974 | Bourgoeis | 156/164 |
| 3,893,879 | 7/1975 | Ito | 156/495 |
| 4,050,462 | 9/1977 | Woon et al. | 128/287 |
| 4,081,301 | 3/1978 | Buell | 156/229 |
| 4,227,952 | 10/1980 | Sabee | 156/494 |
| 4,239,578 | 12/1980 | Gore | 156/229 |
| 4,240,866 | 12/1980 | Rega | 128/290 R |
| 4,261,782 | 4/1981 | Teed | 156/164 |

FOREIGN PATENT DOCUMENTS 2010682 7/1979 United Kingdom .
2011778 7/1979 United Kingdom .

OTHER PUBLICATIONS

Repke et al., "Disposable . . . Manufacture" South Africa Pat. Appl. No. 77/4456 filed Jul. 22, 1976.

Primary Examiner—Jerome W. Massie
Attorney, Agent, or Firm—Leydig, Voit, Osann, Mayer & Holt, Ltd.

[57] ABSTRACT

Methods, the products produced thereby, and apparatus for forming conformable garments having selected discrete elasticized areas. More specifically, methods and apparatus for stretching one or more ribbons of thermoplastic elastomeric material, immobilizing the stretched material in its extended state, subjecting spaced discrete areas of the stretched material to heat so as to "kill" the elastic properties thereof in the heated regions while leaving the elastic properties of the intermediate unheated regions thereof unaltered and bonding the alternate elasticized and non-elasticized zones of the elastic ribbon to a continuous web suitable for use in forming a plurality of interconnected, but severable, like conformable garments having selected discrete elasticized areas on a high speed production basis. In the preferred form of the invention, the conformable garment thus formed comprises a disposable diaper product.

32 Claims, 9 Drawing Figures fig. 1.

METHODS AND APPARATUS FOR ELASTICIZING DISCRETE AREAS OF CONFORMABLE GARMENTS

RELATED APPLICATION

Marion C. Morris, Hugo L. Kons, Randolph J. Hill, and Richard H. Frick, Ser. No. 87,057, filed Oct. 22, 1979, for "Winding Method for Soft Elastomeric Ribbon and Would Spool Resulting Therefrom".

BACKGROUND OF THE INVENTION

The present invention relates in general to methods and apparatus for forming conformable garments having selected discrete elasticized areas on a high speed production basis, and to conformable garments produced thereby; and, more particularly, to forming conformable garments such, for example, as disposable diapers having discrete elasticized areas by stretching a thermoplastic elastomeric material, immobilizing the stretched material in its extended condition, heat treating selected spaced areas of the stretched elastomeric material while in the immobilized extended condition so as to "kill" the elastic properties of the heat treated zones, transferring the immobilized extended material toward a continuously moving web, and affixing the immobilized extended material to the continuous web at production speeds sufficient to produce in excess of 250 diapers per minute while maintaining both the heated non-elasticized zones and the non-heated elasticized zones of the material immobilized with respect to both the transferring means and the continuous moving web. In the preferred form of the invention, the thermoplastic elastomeric material comprises a urethane based material, preferably TUFTANE®, a registered trademark of the manufacturer, B. F. Goodrich General Products Company, Akron, Ohio.

Conventionally, conformable garments having discrete elasticized areas, have been found in a wide variety of ways and utilizing a wide variety of materials. One material commonly employed as the elasticizing element has been natural rubber. Buell U.S. Pat. No. 3,860,003 discloses a disposable diaper formed of such material; while Buell U.S. Pat. No. 4,081,301 describes a process and apparatus for forming such a product. Similarly, Burger U.S. Pat. No. 3,694,815 and Woon et al. U.S. Pat. No. 4,050,462, both assigned to the assignee of the present invention, disclose the use of natural and/or synthetic rubber products to function as an elasticizing element.

Unfortunately, however, natural rubber imposes a number of severe constraints on high speed manufacturing processes. Thus, natural rubber is simply not suitable for storage on support spools because the rubber checks, assumes the shape of the spool, tends to tangle, and binds in the interstices between adjacent underlying loops. Consequently, natural rubber is normally supplied in boxes, with the continuous rubber ribbon being festooned therein. This places a severe limitation on the quantity of material that can be supplied without requiring splicing; and, indeed, at conventional production speeds it is generally necessary to splice such boxes of natural rubber together on the order of every thirty minutes. In addition, since the rubber is festooned in boxes, it tends to tangle and knot as it is removed from the boxes, thereby causing breakage and/or significant amounts of machine down-time. Moreover, natural rubber normally requires talc or other similar lubricants on its surfaces, and such materials seriously interfere with adhesive bonding techniques, thereby necessitating a "detalcing" operation prior to adhesive bonding. Natural rubber is generally rather dark in color and, therefore, when used in garments such as disposable diapers having relatively thin transparent or semi-transparent backing sheets formed of polyethylene or the like, the rubber strips are visible through such material and, therefore, detract from the aesthetic appearance of the product.

It has recently been proposed in published British application No. GB 2 010 682 A, published July 4, 1979, and in published Australian application No. 43750/79, that unvulcanized linear and/or radial block copolymers be utilized as the elasticizing element in conformable garments such as diapers. Such material permits removal of the elastic properties of the block copolymer upon application of heat, ultrasonic, or similar energy inducing means in a manner well known to those skilled in the art.

Over the years, numerous techniques have been developed in the prior art wherein the elastic properties of an elastomeric material are affected by the application of heat. For example, the aforesaid Burger U.S. Pat. No. 3,694,815 assigned to the assignee of the present invention contemplates freezing of an elastic material while the material is in its stretched or extended state so as to immobilize the material while it is being applied to a garment; and, thereafter, thawing the frozen material to restore its elasticity. In Freres et al. British Pat. No. 783,726, the patentee coats a stretched elastic material with a semi-rigid dressing to immobilize the stretched elastic and, thereafter, applied heat to melt the dressing and restore the elastic properties.

Mason U.S. Pat. No. 3,245,407, Althouse U.S. Pat. No. 3,639,917, and Koch U.S. Pat. No. 3,912,565 describe various products and methods wherein selected materials are fastened into a garment and subsequently heated in selected areas thereof while in a contracted or non-stretched condition so as to cause the heated areas to become shirred or elastic in nature—i.e., a heat shrink process used to impart elasticity to selected areas of the garment.

However, despite all of the efforts that have been made to provide a facile, economical process for mass production of conformable garments such, for example, as disposable diapers, problems have, prior to the advent of the present invention, continued to plague the industry. In addition to many of the problems described above with regard to natural rubber—viz., difficulties in feeding continuous runs thereof without tangling, knotting and/or breakage, difficulties in adhesive bonding as a result of surface lubricants, tension uniformity, etc-.—many of the thermoplastic elastomeric materials that have been suggested present similar, as well as somewhat different problems. For example, since the elastic material is here contemplated for usage in garments, it is important that the material be characterized by its strength; not only strength in usage, but also in the high speed manufacturing processes employed. Where the material is to be heat treated to "kill" the elastic properties thereof in selected discrete areas, it is important that the heated material possess sufficient strength as to resist breakage, particularly when the heated material is being worked on in a high speed continuous production process. Color characteristics and adhesive bonding properties have continued to present problems.

SUMMARY OF THE INVENTION

It is the general aim of the present invention to provide improved methods and apparatus which overcome all of the foregoing disadvantages which are characteristic of the prior art, yet which are economical and permit of the manufacture of improved conformable garments on a high speed continuous production basis.

In one of its primary aspects, it is an object of the invention to provide improved methods and apparatus, as well as improved products produced thereby, for forming conformable garments such, for example, as disposable diapers having separate discrete elasticized areas, yet wherein both the elasticized areas and the non-elastic areas of the garment can be formed compatibly with high speed production processes-e.g., processes wherein the garment components are being worked on at speeds sufficient to produce in excess of 250 diapers per minute.

An important object of the invention is the provision of improved methods and apparatus of the foregoing character wherein a suitable thermoplastic elastomeric material can be stretched, immobilized in the stretched condition, and then effectively heat treated in selected spaced discrete areas for the purpose of "killing" the elastic properties thereof in such areas while leaving the elastic properties in other areas unaltered.

It is a further object of the invention to provide improved methods and apparatus for forming conformable garments which minimize machine down-time resulting from splicing requirements and/or breakage, tangling and knotting of elastic materials being fed to the system. In this connection, it is an object of the invention to provide an improved system wherein an elastic material can be readily and effectively spooled in quantities sufficient to permit high speed production runs of on the order of eight hours without the need to splice successive pieces of elastic, and wherein the elastic material may be easily fed to the process equipment without encountering knotting, tangling or breakage.

DESCRIPTION OF THE DRAWINGS

These and other objects and advantages of the present invention will become more readily apparent upon reading the following detailed description and upon reference to the attached drawings, in which.

While the invention is susceptible of various modifications and alternative forms, specific embodiments thereof have been shown by way of example in the drawings and will herein be described in detail. It should be understood, however, that it is not intended to limit the invention to the particular forms disclosed, but, on the contrary, the intention is to cover all modifications, equivalents and alternatives falling within the spirit and scope of the invention as expressed in the appended claims.

DETAILED DESCRIPTION

Figure 1:
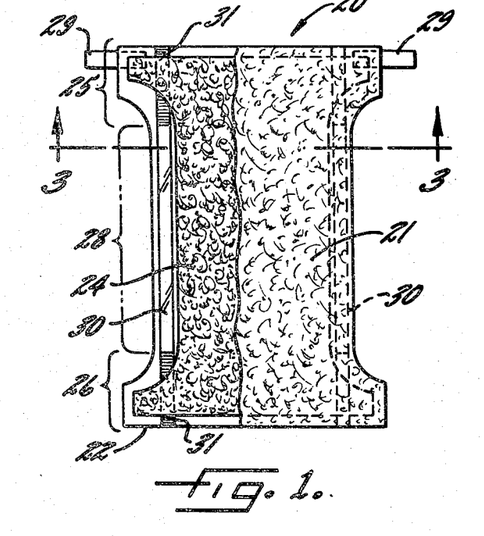
FIG. 1 is a plan view illustrating a conformable garment having discrete elasticized areas and embodying features of the present invention, with the exemplary garment here illustrated comprising a disposable diaper having portions cut away to illustrate construction details, but with the elastically extendible member shown in the fully extended condition which it would normally occupy only during the manufacturing process.
Figure 3:
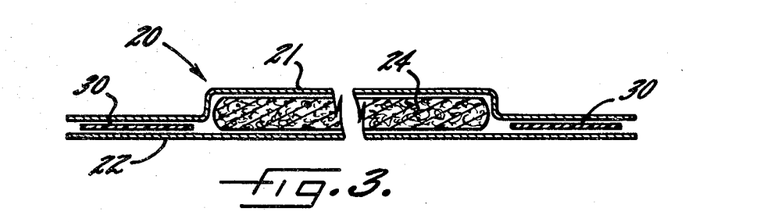
FIG. 3 is a sectional view taken substantially along the line 3—3 in FIG. 1.

Referring first to FIGS. 1 and 3, the present invention has been illustrated in connection with the formation of a conformable garment which is here shown as a disposable diaper, generally indicated at 20. Although the exemplary diaper 20 is here illustrated in the form of a finished product severed from the continuous web of products made in a high speed continuous production operation, it has, for purposes of facilitating a complete understanding of the invention, nevertheless been shown in the stretched or fully extended position that the product would normally occupy just prior to being severed from the continuous web upon completion of the manufacturing process.

In keeping with the present invention, the illustrative diaper 20 is of elongate generally "I" shape, and includes a fluid permeable facing sheet 21, a fluid impervious backing sheet 22, and a highly absorbent batt 24 sandwiched between the facing and backing sheets 21, 22 respectively.

The specific components used to form the exemplary diaper may be any of the types commonly used for such purposes. For example, the fluid pervious facing sheet may be any soft, flexible porous sheet which permits the passage of fluids therethrough including hydrophobic or hydrophilic non-woven webs, wet strength papers, spunwoven filament sheets, and the like. A particularly suitable sheet is one made of spunwoven polypropylene filaments with spot embossing, and preferably with a perforated surface or suitable surfactant treatment to aid fluid transfer. The fluid impermeable backing sheet 22 is preferably a thin plastic film such as polyethylene, polypropylene, polyvinylchloride, or the like and would generally be on the order of one mil in thickness. The sheet is preferably opaque with an embossed or matte surface.

As disclosed in greater detail in the aforesaid Woon et al. U.S. Pat. No. 4,050,462, a suitable material for the absorbent batt 24 used in the exemplary diaper is an air-formed batt of wood pulp fibers commonly known as "fluff". In one preferred example described in the aforesaid Woon et al. patent, the fluff batt weighed about 0.286 grams/sq. in. of area in its unconstricted condition as well as in the planar sections of the batt when the other portions of the diapers are constricted, and about 0.32 grams/sq. in. in the constricted crotch section of the batt. It is preferred that the effective weight of the absorbent material in the constricted crotch area be at least 15% greater per unit area than the weight of the absorbent material in the planar area. The thickness of the same fluff batt in unconstricted condition was measured at about 0.755" and, in constricted condition at about 1.27". The constricted batt, therefore, had more effective thickness in the constricted area. Depending on the size diaper being selected, the starting flat or planar weight and thickness may be suitably varied, i.e., thinner for the smaller sizes, thicker for the larger sizes. Other absorbent materials, alone or in combination and including webs of carded or air-laid textile fibers, multiple plys of creped cellulose wadding, various super absorbent materials, synthetic foam sheets or the like may also be used. The batt may also be slightly compressed or embossed in selected areas as desired.

The exemplary diaper shown in FIG. 1 is divided into waistband sections 25 and 26 at each end and a central narrowed-down crotch section 28 disposed between the waistband sections. During use, waistband section 25 would normally be disposed at the back of the infant and may from time to time be referred to herein as the back portion of the diaper, while section 26 would normally be disposed at the front and may from time to time be referred to herein as the front portion of the diaper. Conventional pressure sensitive tapes 29 are attached to the backing sheet 22 near the edges of waistband section 25 for fastening purposes, although other suitable fastening means may be employed. Such tapes are usually attached near the back portion of the diaper. One surface of absorbent batt 24 is bonded to backing sheet 22 and/or to facing sheet 21 in at least the crotch section 28. Preferably, the absorbent batt is bonded to backing sheet 22 in the crotch section. Such bonding may be done by the use of strips of double-faced pressure sensitive tape, by strips of hot melt or pressure sensitive adhesive, by overall or patterned heat sealing, by a printed pattern of adhesives, or the like. One desirable type of adhesive is an atactic polypropylene based hot melt adhesive of the type known as A337S manufactured by Eastman Chemical Co. of Kingsport, Tennessee. Generally, attachment should be such that when the sheet to which the batt 24 is bonded is constricted in its longitudinal direction by elastic means 30 disposed near the batt edges, the batt will also be constricted and convoluted thereby.

Each edge of the diaper in the narrow crotch section 28 is provided with an elongate elastic means 30 secured in extended condition to backing sheet 22 and/or to facing sheet 21 along the entire length of the crotch section 28. In keeping with the present invention, the free ends 31 of the elastic means 30 positioned in the waistband sections 25, 26 are preferably treated in such a manner as to destroy their elastic properties relative to the backing sheet 22. Such free ends 31 of the elastic means 30 may, if desired, be secured to the backing sheet 22 in the same manner as the elastic means 30.

It should be understood that when it is stated herein that discrete areas of an elastic ribbon or tape are treated to destroy or "kill" the elastic properties of the ribbon in such areas, it is meant simply that the elastic properties in those treated discrete areas are altered so that they no longer exhibit elastic properties relative to their environment. For example, were the treated free end 31 of the elastic ribbon 30 shown in FIG. 1 to be removed from the backing sheet 22, such free end would still exhibit elastic properties and would still be capable of being stretched. However, when released it would return to the length depicted in FIG. 1, and not to its original length prior to treatment. It is in this sense that the elastic properties of the portions 31 are destroyed or "killed", since such portions will not serve to elasticize the garment.

Figure 2:
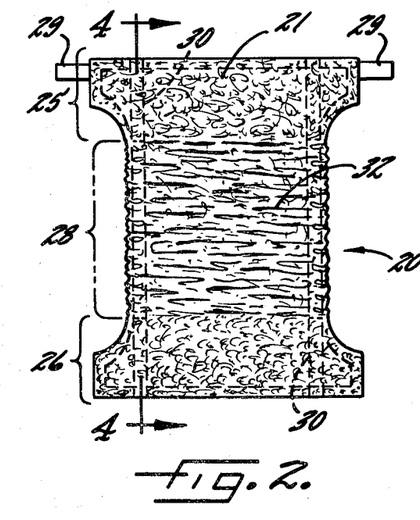
FIG. 2 is a plan view of the exemplary diaper shown in FIG. 1, here illustrating the diaper product following the final separation step in the manufacturing process wherein individualized diapers are cut from a continuous web and with the diaper here being illustrated with the elastically extendible member in its normal relaxed or unextended condition.
Figure 4:
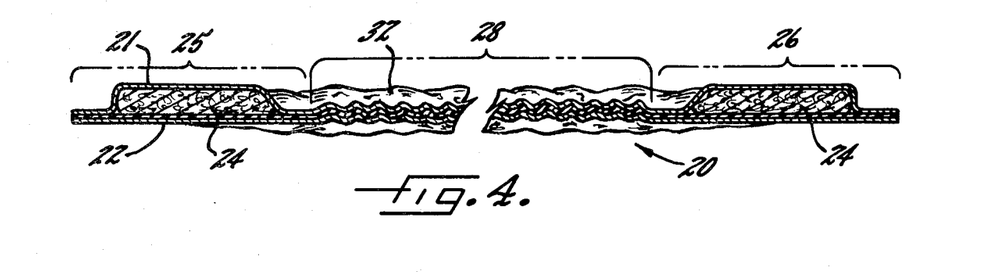
FIG. 4 is a sectional view taken substantially along the line 4—4 in FIG. 2.

As previously indicated, the elastic means 30 is fully stretched and under tension only during the manufacturing process when it exists as a continuous length for convenience in the process. The diaper is shown in its fully extended condition in FIG. 1, a condition which it would normally occupy only during the manufacturing process when a series of diapers are attached to each other in the form of a continuous strip. When this continuous strip is cut into individual diapers, the elastic means 30 is thus relieved of its tension and contracts from its fully extended condition, causing the crotch section 28 of the diaper to contract in the elasticized area as shown in FIGS. 2 and 4. As indicated therein, waistband sections 25 and 26 are not constricted and remain substantially flat or planar because the end portions 31 of the elastic means 30 do not exhibit elastic characteristics relative to the underlying backing sheet 22 and, consequently, there is an absence of a tensioned elastic member in those sections. When the relatively narrow crotch section 28 is constricted by the contracted elastic means 30 at each edge, the crotch section develops a multiplicity of gross transverse rugosities 32. Stated another way, crotch section 28 is reduced in length but still contains the same amount of absorbent material. Accordingly, the absorbent batt 24 in the crotch area 28 is made effectively thicker because bo the adjoining hills and valleys of which the transverse rugosities 32 are comprised and, therefore, will have more absorbent capacity per unit area than a batt of the same original thickness has in its initial planar form.

In addition to making the diaper 20 effectively more absorbent in the crotch area 28, the cushioning effect of the pad element forming the rugosities 32 serves to relieve some of the pressure of the tensioned elastic means 30 where it presses the diaper into contact with the infant's skin when the diaper is worn. Accordingly, even though the elastic means 30 will be under tension in the crotch area 28 due to its being partially stretched out when the diaper is applied to the child, the transverse rugosities 32 remaining in the absorbent pad act as cushions and tend to reduce the possibility of the elastic indenting or marking the skin. Such indentation or marking is more likely to happen when the tensioned elastic means 30 is part of a thin flexible flap as commonly employed in the prior art, thus permitting more intimate contact with the skin.

As heretofore indicated, garments having discrete elastic areas are well known in the art, and many different types of such garments have been described in issued patents. For example, in the aforesaid Buell U.S. Pat. No. 3,860,003, the patentee employs elastic tapes formed of natural rubber. In the aforesaid published British application No. GB 2 010 682 A and published Australian application No. 43750/79, the applicants describe the use of thermoplastic elastomeric members comprising and/or containing unvulcanized linear or radial block copolymers of the general configuration $A^1$-B-$A^2$ and of the type described in Zelinski et al. U.S. Pat. No. 3,281,383.

In accordance with the present invention, however, improved garments having discrete elasticized areas such, for example, as the disposable diaper 20 described above in connection with FIGS. 1-4, are formed with thermoplastic elastomeric ribbons or tapes 30 having a urethane base and, more specifically, from TUFTANE ® and, preferably, from TUFTANE ® Type TF-410, an elastomeric material which has proven to provide tremendous advantages for use in, for example, disposable diapers 20, especially when compared to products employing, for example, elastic bands formed of natural rubber or either linear or radial block copolymers.

Thus, when comparing TUFTANE ® with natural rubber, TUFTANE ® has been found to have more uniform tension properties and to be thinner, softer and more flexible. TUFTANE ® can further be stored on spools in the manner more fully described in the aforesaid application of Morris et al., Ser. No. 087057, filed Oct. 22, 1979, and supplied from such spools, whereas natural rubber generally must be festooned in boxes since, when efforts are made to spool natural rubber, the rubber tends to check to assume the shape of the spool, to tangle, and to bind within the interstices between adjacent ones of the underlying loops on the spool. TUFTANE ®, on the other hand, because it can be spooled, substantially eliminates tangles, knots and breaks in high speed production processes, and can be stored on spools in sufficient quantities which permit operation of production runs up to and in excess of eight hours without the need to splice the TUFTANE ® bands; whereas, festooned natural rubber generally requires splicing between successive boxes every thirty or so minutes at normal production speeds. TUFTANE ® further permits of destruction of its elastic properties relative to its environment, whereas natural rubber does not. Because TUFTANE ® can be obtained in colorless form, those products such as disposable diapers which commonly employ a relatively thin transparent or semi-transparent backing sheet 22 formed of polyethylene or the like, have a much more pleasing aesthetic appearance.

When contrasted with other thermoplastic elastomeric materials such, for example, as block copolymers, TUFTANE ® has proven to have similar advantages. Thus, it permits ease and simplicity of process control since the elastic properties can be effectively 100% "killed" relative to the environment over a relatively wide range of temperatures and, further, TUFTANE ® is very strong and does not tend to break or tear easily either in the overall high speed production process utilized or in the heat treating "kill" process used to destroy its elastic properties relative to the environment in selected discrete areas. TUFTANE ® further exhibits excellent adhesive bonding properties and posseses a high coefficient of friction which is essential to prevent slippage of the elastic ribbons during the manufacturing process, especially when intermittent spaced discrete areas of the ribbon are subjected to heat to "kill" the elastic properties of the ribbon in such areas. As in the case of natural rubber, the availability of colorless TUFTANE ® remains a distinct advantage over many other types of thermoplastic elastomers which are not colorless and, therefore, which tend to detract from the aesthetic appearance of products such as disposable diapers.

Thus, referring to FIGS. 1-4, and in accordance with the present invention, the elastic means 30 comprises a strip or ribbon of TUFTANE ®, preferably on the order of 1.5 mils in thickness and on the order ½" in width, wherein the end portions 31 have been heated so as to destroy or "kill" the elastic properties of the ribbon relative to the facing and/or backing sheets 21, 22 to which the ribbon has been attached. As a consequence, when the individual diapers 20 are severed from the continuous web of interconnected diapers formed in a manufacturing process, the central portions of the TUFTANE ® ribbons which are co-extensive with the crotch section 28 and which have not been subjected to sufficient heat to "kill" or otherwise deleteriously affect the elastic properties thereof, tend to contract, thus forming the transverse rugosities 32 in the diaper as best illustrated in FIGS. 2 and 4; whereas, the waistband portions 25, 26 of the diaper 20 remain substantially planar and are not contracted since the end portions 31 of the TUFTANE ® ribbon have had the elastic properties thereof effectively "killed" in the manufacturing process by the application of heat thereto.

In accordance with another of the important aspects of the present invention, provision is made for affixing thermoplastic elastomeric strips on selected separate discrete areas of a continuous web suitable for use as a portion of a conformable garment on a high speed, continuous, production basis. In the preferred form of the invention, methods and apparatus are provided for affixing one or more TUFTANE ® ribbons 30 to a continuous web or sheet of material suitable for use as the backing sheets 22 for a series of interconnected diapers where the continuous web is moving at a relatively high speed—e.g., speeds sufficient to produce in excess of 250 diapers per minute—yet, where the TUFTANE ® ribbons 30, although also moving at the same relatively high speed, are immobilized relative to a surface moving at that speed and having at least one heated "kill" zone and at least one unheated "no-kill" zone; whereby the elastic properties of the ribbon are destroyed in the heated "kill" zone but remain unaltered in the unheated "no-kill" zone. In the exemplary form of the invention, the elastic properties of the TUFTANE ® ribbons 30 are selectively "killed" in spaced discrete areas just prior to being affixed to the continuous web.

Figure 5:
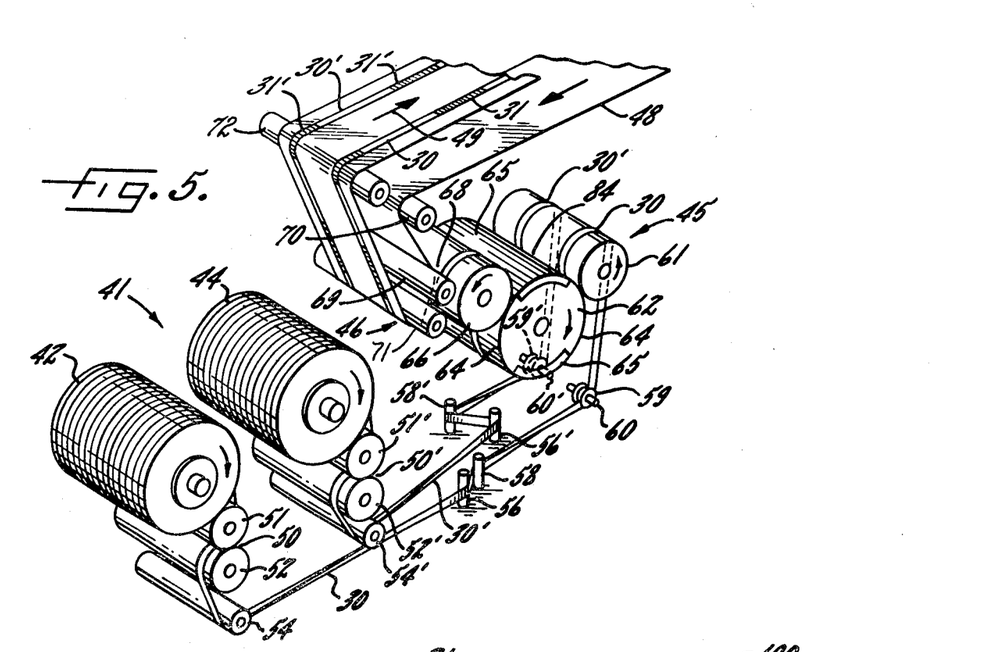
FIG. 5 is a diagrammatic perspective view of a system embodying features of the present invention suitable for applying elastically extendible members to a continuous web which forms part of a garment during a continuous high speed production operation so as to elasticize discrete areas of the web and, thus, of the garment to be formed, with the elasticized discrete areas here being shown in the fully extended condition as normally occupied during the manufacturing process.

To accomplish the foregoing objectives of the invention, and as illustrated diagrammatically in FIG. 5, a system, generally indicated at 40, is provided having a supply stand, generally indicated at 41, for level-wound spools 42, 44 of a suitable thermoplastic elastomeric material, preferably TUFTANE ®, level-wound thereon in the form of continuous TUFTANE ® ribbons 30, 30'. The TUFTANE ® ribbons 30, 30' are fed from the supply stand 41 through a selective heat treating zone, generally indicated at 45, and then to an area, generally indicated at 46, where the ribbons 30, 30' are affixed to a continuous web 48 moving at the selected high production speed—e.g., at a speed sufficient to produce in excess of 250 diapers per minute. The web 48 may be fed from any suitable conventional source (not shown) to and through the area 46 where the TUFTANE ® ribbons 30, 30' are affixed; and to further conventional web processing areas (not shown in FIG. 5, but located downstream as indicated by arrow 49 and as hereinafter described) where the composite web and TUFTANE ® may be assembled with a series of absorbent batts 24 (FIG. 1) and a continuous web defining interconnected fluid permeable facing sheets 21 such as shown in FIG. 1, to form a continuous sandwich (of the type shown in FIGS. 1 and 3) suitable for forming a plurality of disposable diapers upon being severed transversely of the sandwich in any conventional manner (not shown).

As here shown, the spools 42, 44 holding continuous TUFTANE ® ribbons 30, 30', respectively, are preferably level-wound in the manner described in greater detail in the aforesaid application of Morris et al., Ser. No. 087057, filed Oct. 22, 1979. Each of such spools is capable of holding a sufficient quantity of TUFTANE ® ribbon approximately 1.5 mils thick and on the order of ½ in width to supply a production line operating at a speed sufficient to produce in excess of 250 diapers per minute for up to eight hours. Thus, the ribbon 30 carried by, for example, spool 42 is unwound therefrom and passed through a nip 50 defined by an idler roll 51 and a driven roll 52 and, thereafter, about a second idler roll 54. To ensure that the ribbon 30 is properly registered with the web 48, the ribbon 30 is twisted 90° after passing around idler roll 54, and is fed between a pair of spaced, upright guide rollers 56, 58. Roller 58 is aligned in the machine direction with a pulley or sprocket 59 affixed to a magnetic powered tension read-out roller 60. During transit from guide roller 58 to sprocket 59, the ribbon is retwisted 90° so as to pass smoothly around the sprocket 59. In precisely the same fashion, the TUFTANE ® ribbon 30' from spool 44 is fed through a nip 50' defined by an idler roll 51' and a driven roll 52', around a second idler roll 54', through a pair of upright guide rollers 56', 58', and around a second sprocket 59' carried by tension read-out roller 60'.

In order to "kill" the elastic properties of the TUFTANE ® ribbons 30, 30' in selected, spaced discrete areas in accordance with the present invention, the ribbons 30, 30' are fed in parallel about a suitable roll 61 and about the periphery of a driven roll 62 having a peripheral surface defining alternate heated zones 64 and non-heated zones 65. Thus, the driven roll 62 defines a high speed moving surface having a pair of heated "kill" zones 64 alternating with a pair of unheated "no-kill" zones 65. The ribbons 30, 30' are in intimate face-to-face contact with the roll 62 throughout approximately 270° of the surface of the roll. In order to ensure that there is no relative slippage between the driven roll 62 and the ribbons 30, 30', the unheated zones 65 are preferably formed of an inherently non-slip material such, for example, as soft silicone foam rubber. Immobilization of the ribbons 30, 30' relative to the driven roll 62 is essential in order to ensure that the alternate areas 30, 31' of the ribbons do not slip as a result of the elastic properties which are retained in those areas of the ribbons overlying the unheated "no-kill" zones 65.

While the exemplary system 40 shown diagrammatically in FIG. 5 has been illustrated as including heated zones 64 which extend across the full width of the roll 62, it is not necessary to heat that extensive a surface area of the roll. Rather, it is only necessary to heat a pair of relatively narrow circumferential bands somewhat wider than the ribbons 30, 30' so as to minimize the need to provide perfect registration between the ribbons 30, 30' and narrow heated circumferential bands. Heating only narrow circumferential bands rather than the full width of roll 62 in the heated zones 64 serves to minimize heat transfer to adjacent components of the apparatus such, for example, as the roll 61 previously described or a driven take-off roll 66.

Following selective heat treatment of spaced discrete areas of the immobilized elastic ribbons 30, 30', the ribbons are transferred to a take-off roll 66 which also serves as a chill roll. To insure that the ribbons 30, 30' remain immobilized until bonded to the continuous web 48, the take-off or chill roll 66 is provided with a high-friction, non-slip surface such, for example, as a surface formed of soft silicone foam rubber. The chill roll 66 serves to prevent heat build-up in the unheated zones 65 of roll 62, to cool the heat treated portions of the ribbons 30, 30', and to prevent or minimize heat transfer to those portions of the system used to convey the continuous web 48. A fine bead of adhesive is preferably applied to the exposed surfaces of the ribbons 30, 30' as they are carried about roll 66 in immobilized fashion by any suitable adhesive applying means (not shown in FIG. 5, but hereinafter described in greater detail). After application of adhesive thereto, the still immobilized ribbons enter a nip 68 defined by roll 66 and an idler roll 69.

To permit adhesive bonding of the ribbons 30, 30' to the continuous web 48, the web is passed around idler roll 70, through the nip 68 defined by idler roll 69 and roll 66, and then around edler rolls 71, 72 and downstream (not shown in FIG. 5) on the production line where the web is formed into a sandwich such as shown in FIG. 3 comprising outer or fluid impermeable backing sheets 22 (formed from web 48), a plurality of spaced absorbent batts 24, and a second continuous web defining the fluid permeable facing sheets 21. As the web 48 enters the nip 68, it comes into contact with the adhesively coated immobilized ribbons 30, 30' which are carried by roll 66 and is securely bonded thereto by pressure applied by idler roll 69. As a consequence, the web 48 and elastic ribbons 30, 30' together with their alternating heat treated non-elastic portions 31, 31' exit from the idler roll 69 and are transported as a composite unit with the elastic portions 30, 30' still fully extended about the idler rolls 71 and 72 for further processing in the manner described above. When the continuous diaper sandwich has been completely formed, the sandwich is severed transversely through the mid-points of the heat treated, non-elasticized areas 31, 31' so as to form a plurality of diapers 20 of the type shown in FIG. 2.

Thus, those skilled in the art will appreciate that there has herein been described a rather simple, economical process and apparatus for elasticizing separate discrete areas of a garment wherein one or more ribbons of elastic material are prestretched to a desired extended state, immobilized in that extended state, and spaced selected discrete areas of the thus extended and immobilized elastic ribbon(s) are then heated to "kill" the elastic properties thereof. Adhesive is then applied to the immobilized ribbon(s) which is (are) then brought into intimate face-to-face contact with a continuous web moving at high speed and adhesively bonded thereto. More specifically, at least those portions of the ribbon(s) intermediate the heat treated areas—i.e., those portions of the ribbon(s) which still retain their elastic properties—are bonded to the selected discrete garment areas to be elasticized while maintaining the ribbon(s) relatively immobilized with respect to both the high friction surface of roll 66 and the discrete garment areas so that upon removal of the composite garment and adhesively bonded ribbon(s) from the high friction surface of roll 66 and, where and if required, upon completion of any further downstream processing and/or assembly steps (not shown), those portions of the stretched ribbon(s) intermediate the heated areas are permitted to relax, thereby elasticizing the discrete selected areas of the garment.

Figure 6:
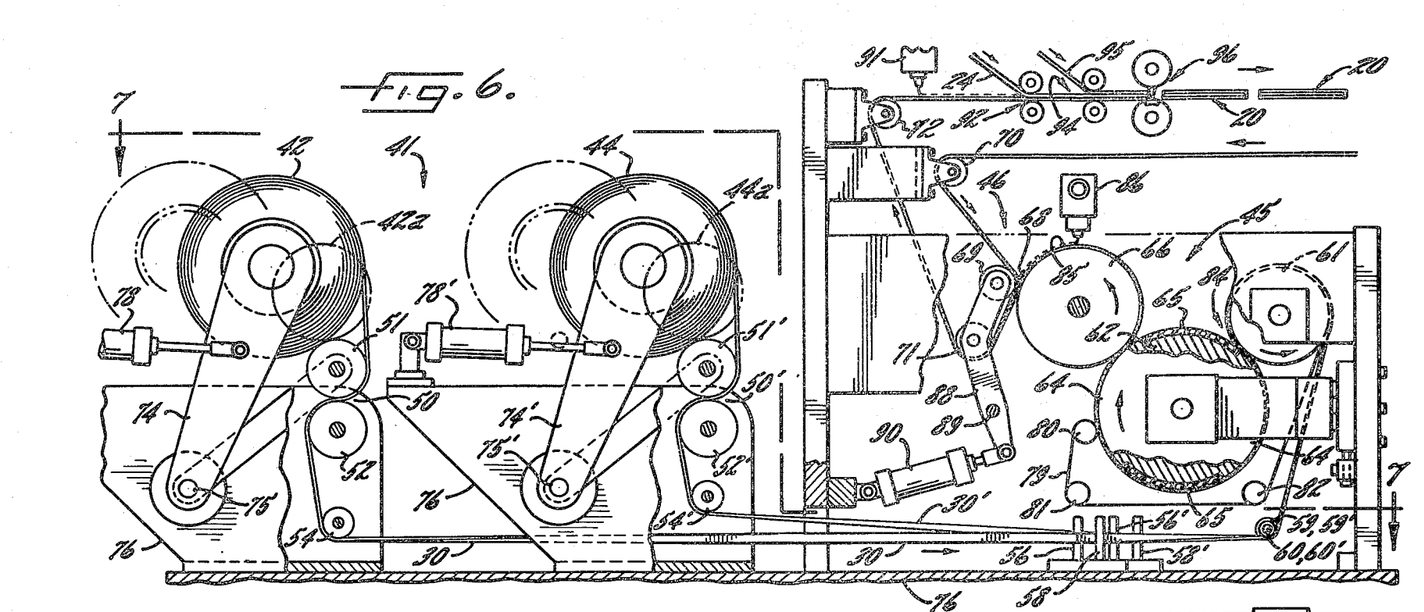
FIG. 6 is a side elevational view, partly in section and partly in diagrammatic form, here illustrating details of an exemplary high speed continuous production system embodying features of the present invention which is suitable for applying elastically extendible continuous ribbons in an extended state to a continuous web and wherein provision is made for destroying the elastic character of the elastically extendible ribbons in selected discrete areas so that only other selected discrete areas of the continuous web are elasticized.
Figure 7:
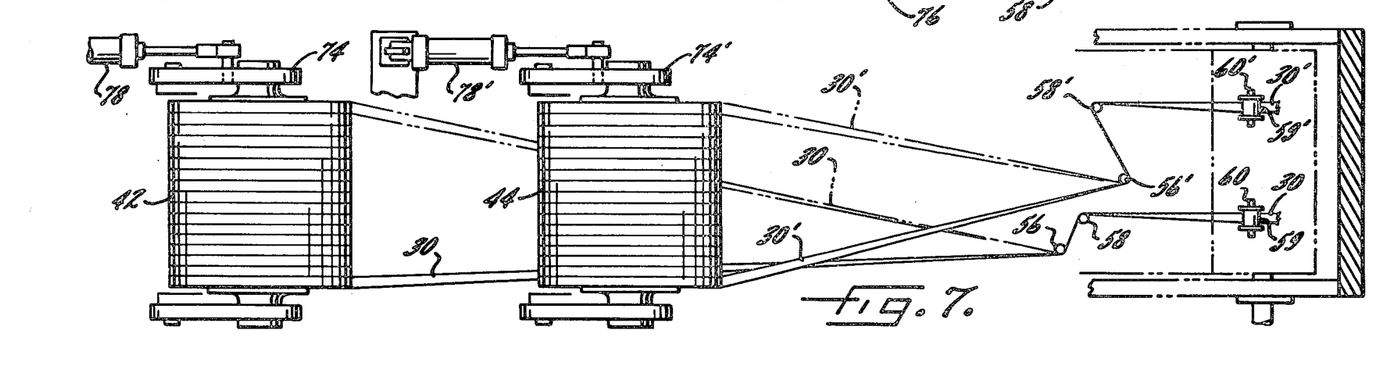
FIG. 7 is a plan view partly in section and taken substantially along the line 7—7 in FIG. 6, here illustrating details of the elastic ribbon supply system utilized with the apparatus shown in FIG. 6.

Turning to FIGS. 6 and 7, an exemplary system embodying features of the invention has been shown in considerably greater detail. Thus, as here shown, it will be observed that the spools 42, 44 of level-wound TUFTANE® are each removably carried by a pair of support arms 74, 74' which are respectively pivotly mounted at 75, 75' to the frame 76 of the apparatus. In order to facilitate removal of empty spools and replacement thereof with fully loaded level-wound spools, the spool support arms 74, 74' are respectively coupled to double-acting fluid operated cylinders 78, 78' which are operated by any suitable fluid control means (not shown). The arrangement is such that when the operator desires to replace the spools, it is merely necessary to pressurize the cylinders 78, 78' so as to pivot the pairs of arms 74, 74' counterclockwise (as viewed in FIG. 6) to a spool removal position. When the empty spools have been removed and replaced with fully loaded spools, the cylinders 78, 78' are again pressurized so as to pivot the arms 74, 74' clockwise until the spools 42, 44 respectively engage idler rolls 51, 51'. At this point, the cylinders 78, 78' may, if desired, be depressurized since the weight of the spools 42, 44 is sufficient to maintain the spools in engagement with the idler rolls 51, 51' as the TUFTANE® ribbons 30, 30" are unwound. As best shown in FIG. 6, as the TUFTANE® ribbons 30, 30" are unwound from the spools 42, 44, the outside diameters of the spools are reduced. Consequently, the weight of the spools serves to insure that the spools slowly pivot in a clockwise direction as viewed in FIG. 6 about pivot points 75, 75' until such time that the spools are empty—here illustrated by the phantom line representations 42a, 44a for the empty spools.

The function of the guide rolls 56, 58 and 56', 58' to insure proper registration of the ribbons 30, 30' is best illustrated upon reference to FIG. 7. As here shown, it will be noted that the ribbon 30, for example, is initially being unwound from the lower portion of level wound spool 42 as viewed in the drawings and as indicated by the solid line representation for the ribbon 30. As the spool unwinds, the point of departure of the ribbon 30 from the spool traverses the full width of the spool as represented by comparison of the solid line and phantom line representations of ribbon 30. But, irrespective of where the point of departure is from the spool 42, the ribbon 30 passes around upstanding guide rollers 56, 58 which are free to rotate about fixed vertical axes. Consequently, the ribbons 30, 30' are properly aligned in the machine direction as they pass around guide rollers 58, 58' and are fed around sprockets 59, 59' on the tension read-out rollers 60, 60' (FIG. 6).

In the form of the invention illustrated in FIG. 6, provision is made for further insuring that the ribbons 30, 30' are maintained immobilized relative to the roll 62 during the selective "heat-kill" process. To accomplish this, an endless nip belt 79 is trained about roll 61, about approximately 220° of the peripheral surface of roll 62, and about a series of idler rolls 80, 81 and 82. The arrangement is such that the ribbons 30, 30' pass over nip belt 79 as it passes around roll 61 and enter the nip 84 between the nip belt 79 and roll 62. Consequently, the nip belt 79 serves to hold the ribbons 30, 30' snugly against the peripheral surface of the roll 62 and, thereby assists in immobilizing the ribbons 30, 30' relative to the surface of roll 62. It has been found that the use of a nip belt to assist in immobilizing the ribbons relative to the selective "heat-kill" surface is highly beneficial when working at relatively high speed operation with a roll 62 which, as here, is on the order of 11.14" in diameter. However, such a nip belt has not been found necessary when operating with smaller rolls 62.

As previously indicated, after selective heat treatment by the spaced heated portions 64 of the peripheral surface of roll 6, the ribbons 30, 30' are passed over a chill roll 66 and enter the nip 68 between roll 66 and idler roll 69. Chill roll 66 serves to insure that any heat transferred from the heated portions 64 of roll 62 to the surface of the chill roll is effectively withdrawn so as to prevent heating of the chill roll which could damage the polyethylene web 48. The particular means employed for effecting cooling of the chill roll is not critical to the present invention and has not been illustrated herein. Any suitable well known conventional cooling means may be employed such, for example, as continuous passage of room temperature water through the chill roll 66.

In order to effect a firm bond between the heat treated ribbons 30, 30' and the web 48, a continuous fine bead 85 of hot melt adhesive is applied to the upper surfaces of the ribbons 30, 30' by means of a suitable adhesive extruder 86. Such hot melt adhesive may take any suitable form. However, excellent results have been achieved with a hot melt adhesive manufactured by H. B. Fuller Company, St. Paul, Minnesota and identified as HM 1533, an adhesive containing a suitable hot melt synthetic rubber material available from Shell Chemical Company, Cleveland, Ohio and designated "Kraton". When the ribbons 30, 30' enter nip 68, the fine adhesive beads 85 contact the surface of the continuous web 48 of polyethylene or the like, thus firmly bonding the ribbons to the web. Since chill roll 66 is covered with a suitable non-slip surface such, for example, as a soft silicone foam rubber material, the alternating fully extended elastic portions 30, 30' and the heat treated extended but non-elastic portions 31, 31' which no longer exhibit elastic properties relative to their environment are maintained in an immobilized state until adhesive bonding to the web 48.

To insure effective bonding of ribbons 30, 30' to web 48, provision is made for biasing the roll 69 into engagement with chill roll 66. To this end, the idler rolls 69, 71 are mounted on a pair of bell cranks, one such bell crank being illustrated at 88 in FIG. 6. The bell cranks 88 are pivotly mounted at 89 to the frame 76 of the apparatus. A suitable fluid actuated double-acting cylinder 90 is provided for controllably pivoting the bell cranks 88 in a clockwise direction as viewed in FIG. 6 about pivot point 89, thus urging the idler roll 69 into intimate engagement with chill roll 66 so as to insure that an effective bond is established between the adhesively coated ribbons 30, 30' and web 48.

In operation, provision is made for stretching the elastic ribbons 30, 30' to a desired extended stretched condition prior to selectively "heat-killing" the elastic properties of alternate discrete areas thereon. To accomplish this, the driven rolls 52, 52' in the elastic ribbon supply stand 41 are preferably operated at a surface velocity considerably slower than the driven rolls 62, 66 in the heat treating zone 45. Consequently, the elastic ribbons 30, 30' are stretched between the respective drive rolls 52, 52' and roll 62, thereby providing fully extended stretched elastic ribbons 30, 30' entering nip 84 between roll 61 and roll 62 and exiting from roll 62. The degree of stretch may be varied by adjusting the surface speed differential between the pairs of driven rolls 52, 52' and driven roll 62. Typically, the speed differential would be set so that the elastic ribbons 30, 30' are stretched on the order of about 100% of their original unextended length; this degree of stretch normally insuring comfortable wear of garments to which elastic ribbons 30, 30' are attached. The degree of stretch as referred to above and hereinafter is defined as:

$$\frac{L_1 - L_0}{L_0} \times 100\%$$

where $L_1$ is the stretched length and $L_0$ is the length of the elastic ribbon in its normal contracted state.

In carrying out this aspect of the present invention, the "heat-kill" roll 62 and chill roll 66 are preferably interconnected by a suitable conventional gear train (not shown) so as to insure synchronous driving thereof at the selected operating speed of the high speed production line, and are driven at a speed on the order of twice the speed of driven rolls 52, 52'. For example, assuming operation of the production line at a speed of x f.p.m. (where x is preferably controlled to produce in excess of 250 diapers per minute), the rolls 62, 66 are driven at a synchronous surface speed of x f.p.m., while rolls 52, 52' are driven at approximately x/2 f.p.m. Tension read-out rolls 60, 60' serve to continually measure the tension of the respective stretched elastic ribbons 30, 30' in a manner well known to those skilled in the art and may, therefore, be used in a conventional feedback servo system (not shown) to respectively adjust the surface speeds of driven rolls 52, 52' to insure that the desired degree of stretch—e.g., 100% stretch—is maintained.

In operation, it has been found desirable to heat the portions 64 of the roll 62 to temperatures in the range of 175°–225° F. Each increment of the elastic ribbons 30, 30' will preferably have a dwell time on the order of at least .225 seconds while immobilized relative to roll 62; such dwell time being sufficient to achieve 100% "kill" of the elastic properties of the areas of the ribbons 30, 30' engaged with the heated portions 64 of roll 62 at any temperature within the range of 175°–225° F. Of course, at slower speeds, dwell time would be increased. However, in the event that it is necessary to stop the machine for any given reason, temperatures on the order of only 175°–225° F. are not sufficient to melt or otherwise damage the elastic TUFTANE® ribbons 30, 30' during the period of down time, but they are sufficient to "kill" the elastic properties of those portions of the ribbons that are contact with the heated portions 64 of roll 62 provided that the dwell time equals or exceeds 0.225 seconds.

Those skilled in the art will appreciate that there have herein been described methods and apparatus suitable for effectively destroying the elastic properties of a fully extended, stretched elastic ribbon in spaced discrete areas while maintaining the ribbon immobilized, and for then affixing the fully extended ribbon to a continuous web while maintaining the ribbon in its immobilized extended state relative to the web. As a consequence, the web and ribbon composite will be effectively elasticized in those areas where the elastic ribbon was in contact with the unheated high friction surface areas 65 on roll 62; yet, in those areas 31 of the stretched elastic ribbon which contacted the heated or "kill" zones 64 on roll 62, the elastic properties of the ribbon relative to the roll 62 and, therefore, relative to the web 48 to which the ribbon is attached, are effectively destroyed; thus insuring that the web 48 is effectively elasticized in those discrete areas where it is bonded to the unheated portions 30 of the elastic ribbons, but is not elasticized in those discrete areas where it is bonded to the previously heated portions 31 of the elastic ribbons.

While the present invention has herein been described in connection with methods and apparatus for applying a continuous fine bead 85 of a suitable hot melt adhesive to the surface of the extended elastic ribbon 30, it is not necessary to provide a continuous adhesive bond between the ribbon 30 and the web 48. Rather, all that is necessary is that those areas of the ribbon 30 which are intended to remain elastic be adhesively bonded to the web either continuously, intermittently, and/or at the points of demarcation between the elasticized and non-elasticized areas of the ribbon; or, alternatively, that those areas 31 where the elastic properties of the ribbon have been altered be adhesively bonded to the web either continuously, intermittently, and/or at the points of demarcation between the elasticized and non-elasticized areas of the web. However, in the preferred embodiment of the invention wherein the methods and apparatus herein described are used to form a disposable diaper 20 (FIG. 2), it is preferred that at least the unheated elastic areas of the ribbons 30, 30' be adhesively secured to the backing sheets 22 defined by web 48 throughout the entire elasticized crotch portions 28 (FIGS. 1, 3 and 4) of each diaper 20, although such adhesive bonding may be either continuous as shown in FIG. 6, or intermittent (not shown).

Those skilled in the art will further appreciate that the selected discrete areas of the elastic ribbon which are to be heated so as to kill their elastic properties could, if desired, be heated after being adhesively secured to the continuous web 48. In such an arrangement (not shown), it would simply be necessary to feed the continuous web 48 into the nip between nip belt 79 and the ribbons 30, 30' as they are delivered to roll 61 (Cf., FIG. 6). In such an arrangement, however, it would be necessary to insure essentially perfect registration of the elastic ribbons with the heated portions 64 of the roll 62: i) to ensure that the elastic properties of the ribbons are "killed" throughout the entire widths of the ribbons in the selected areas 31 (FIGS. 1 and 5), and ii) to prevent direct application of heat to the surface of the web 48.

Once the composite of web 48 (which preferably comprises a series of interconnected diaper backing sheets 22—see, e.g., FIGS. 1 and 3) and the thermoplastic elastomeric ribbons 30, 30' has been formed, the composite may then be passed through subsequent conventional downstream work areas for further processing. In the case of formation of, for example, a disposable diaper 20 of the type shown in FIGS. 1-4, the composite web 48 and elastomeric ribbons 30, 30' would preferably first be passed beneath suitable adhesive extruding means (such as that indicated diagrammatically at 91 in FIG. 6) where a plurality of closely spaced fine lines of adhesive are continuously applied longitudinally of the composite. Thereafter, the composite is preferably passed through an area (such as that shown diagrammatically at 92 in FIG. 6) where suitable absorbent batts 24 are deposited on the composite. In the exemplary apparatus, the "open-face" sandwich of web 48, ribbons 30, 30', adhesive glue lines, and spaced discrete absorbent batts 24 is then passed through a further area (diagrammatically indicated at 94 in FIG. 6) where a continuous web 95 comprising a plurality of interconnected fluid permeable facing sheets 21 (See, e.g., FIGS. 1 and 3) is superimposed on the sandwich and adhesively bonded to the exposed portions of the backing sheets 22 by the parallel longitudinal glue lines deposited by the extruder 91. Finally, the thus formed completed continuous sandwich of interconnected diapers is passed through a suitable cutting area (diagrammatically indicated at 96 in FIG. 6) where the composite is severed transversely so as to separate successive diapers, thereby permitting the non-heated elasticized portions of ribbons 30, 30' to contract and forming elasticized diapers such, for example, as that shown in FIGS. 2 and 4.

Figure 8:
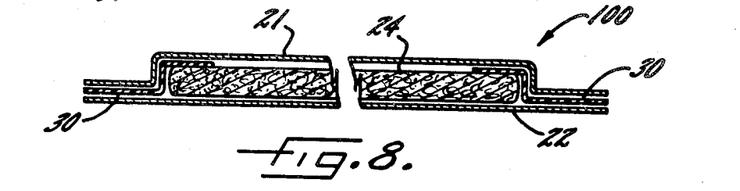
FIG. 8 is a sectional view similar to FIG. 3, but here illustrating a slightly modified disposable diaper product which can be made in accordance with the present invention; and, FIG. 9 is a plan view of a partially completed disposable diaper product, here illustrating an alternative embodiment of the invention wherein the selectively elasticized areas of the continuous web can be formed with a shaped configuration so as to improve the conformability of the finished diaper product.

Turning now to FIG. 8, there has been illustrated a slightly modified form of the invention wherein a diaper sandwich 100 is illustrated having a fluid permeable facing sheet 21, a fluid impermeable backing sheet 22, an interposed absorbent batt 24, and elastic ribbons 30 which are not only secured to the backing sheet 22 but, also, overlie the marginal edges of the absorbent batt 24. Thus, in this embodiment of the invention, the elastic ribbons function not only as elasticizing elements but, also, as an additional moisture barrier.

Figure 9:
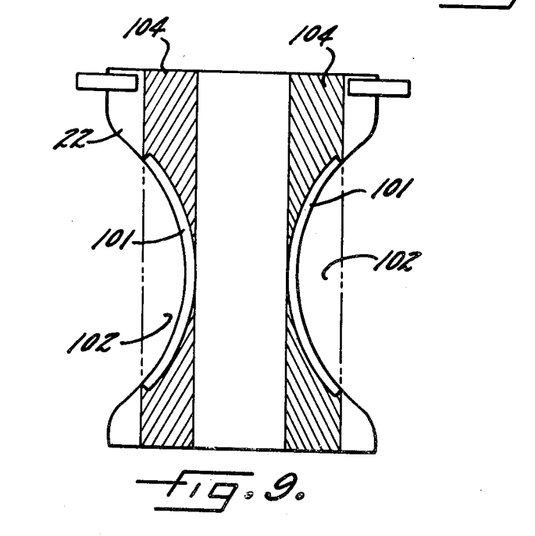

Yet another modification of the invention has been illustrated in FIG. 9 wherein the elastic TUFTANE ® ribbons are somewhat wider than hereinabove described —e.g., the ribbons have a width on the order of approximately 2". In this form of the invention, the heated portions 64 of the roll 62 would be shaped (not shown in the drawings) so as to subject the ribbons to heat throughout virtually the entire length of each ribbon except for a curved portion represented in FIG. 9 by the reference numerals 101, 102. Thus, the shaded area 104 of the elastic ribbons would be subjected to heat to effectively "kill" the elastic properties thereof relative to the backing sheet 22, while the areas 101 and 102 are not heated and remain elastic. Subsequently, the area 102 would be cut away so as to provide a diaper having a shaped elastic leg or crotch portion where the elastic portion 101 is curved and on the order of ½" in width. As a consequence of the curved nature of the elastic portion 101, the diaper will conform more readily to the leg of the infant.

I claim:

1. A method for forming a conformable garment having one or more discrete elasticized areas comprising the steps of:
    (a) stretching one or more ribbons of thermoplastic elastomeric material;
    (b) immobilizing the stretched material in its extended state;
    (c) subjecting spaced discrete areas of the stretched immobilized material to heat so as to "kill" the elastic properties thereof in the spaced heated areas while leaving the elastic properties of the intermediate unheated areas thereof unaltered; and,
    (d) bonding at least one of the alternate elasticized and non-elasticized areas of the stretched immobilized elastic ribbon to a continuous moving web suitable for use in forming a plurality of interconnected, but severable, like conformable garments having selected discrete elasticized areas on a high speed production basis.

2. The method as set forth in claim 1 further characterized in that the thermoplastic elastomeric material is a urethane.

3. The method as set forth in claim 1 wherein the conformable garment is a diaper having a fluid pervious facing sheet, a fluid impervious backing sheet, and an intermediate absorbent batt sandwiched therebetween with the peripheral portions of the facing and backing sheets secured together, and wherein the continous moving web defines a plurality of interconnected diaper facing or backing sheets, and further characterized in that the stretched immobilized material is bonded to the web along the opposed edges of the diaper sheets and is heated in those spaced discrete areas bonded to the waistband areas of the diaper sheet while those areas bonded to the opposed edges of the crotch sections of the diaper sheets are unheated areas of elastomeric material whereupon severing of the web intermediate the interconnected diaper sheets permits the unheated portions of the elastomeric material to contract, thereby elasticizing the crotch section of the diaper.

4. Apparatus for forming a conformable garment having one or more discrete elasticized areas comprising, in combination: means for stretching at least one ribbon of thermoplastic elastomeric material; means for immobilizing the stretched material in its extended state; means for bonding the immobilized stretched ribbon to a continuous moving web suitable for use in forming a plurality of interconnected, but severable, like conformable garments having at least one selected discrete elasticized area on a high speed production basis; and means for heating spaced discrete areas of the immobilized stretched material so as to "kill" the elastic properties thereof in the spaced heated areas while leaving the elastic properties of the intermediate unheated areas thereof unaltered so that upon severing the web a plurality of like conformable garments are formed each having at least one discrete elasticized area contiguous with the unheated areas of the elastic ribbon bonded thereto.

5. The combination as set forth in claim 4 wherein means are provided for stretching a pair of ribbons of thermoplastic material and for immobilizing and bonding the stretched pair of ribbons to a continuous moving web in their immobilized stretched condition and along spaced parallel lines and wherein said heating means is adapted to heat selected spaced discrete areas of both ribbons.

6. Apparatus for forming a conformable garment having one or more discrete elasticized areas comprising, in combination: means for stretching at least one ribbon of thermoplastic elastomeric material; means for immobilizing the stretched material in its extended state; means for heating spaced discrete areas of the immobilized stretched material so as to "kill" the elastic properties thereof in the spaced heated areas while leaving the elastic properties of the intermediate unheated areas thereof unaltered, and means for bonding the alternate elasticized and non-elasticized areas of the immobilized stretched elastic ribbon to a continuous moving web suitable for use in forming a plurality of interconnected, but severable, like conformable garments having at least one selected discrete elasticized area on a high speed production basis.

7. A method for forming a conformable garment having one or more discrete elasticized areas on a high speed production basis comprising the steps of:
 (a) stretching a thermoplastic elastomeric material;
 (b) immobilizing the stretched material in its extended condition;
 (c) heat treating selected spaced zones of the stretched elastomeric material while in the immobilized extended condition so as to "kill" the elastic properties of the heat treated zones while leaving the elastic properties of the intermediate unheated zones unaltered;
 (d) affixing the immobilized extended material to a continuous moving web defining a plurality of interconnected conformable garment components while maintaining both the heated non-elasticized zones and the non-heated elasticized zones of the extended material immobilized with respect to both the transferring means and the continuous moving web; and,
 (e) severing the web transversely thereof between adjacent ones of the plurality of interconnected conformable garment components so as to form a plurality of separate garment components each having at least one discrete elasticized area contiguous with the unheated zones of the elastic material affixed thereto.

8. The method as set forth in claim 7 further characterized in that the thermoplastic elastomeric material a urethane.

9. The method as set forth in claim 8 wherein the selected spaced zones of the elastomeric material are heated at a temperature in the range of 175° F. to 225° F.

10. The method as set forth in claim 8 wherein the comformable garment is a disposable diaper.

11. Apparatus for forming a conformable garment having one or more discrete elasticized areas on a high speed production basis comprising, in combination: means for stretching a thermoplastic elastomeric material; means for immobilizing the stretched material in its extended condition; means for transferring the immobilized extended material toward a moving web; means for affixing the immobilized extended material to a continuous moving web defining a plurality of interconnected conformable garment components while maintaining the immobilized extended material in its immobilized extended condition relative to both said transferring means and the web; means for heat treating selected spaced zones of the stretched elastomeric material while in the immobilized extended condition so as to "kill" the elastic properties of the heat treated zones while leaving the elastic properties of the intermediate unheated zones unaltered; and, means for severing the web transversely thereof between adjacent ones of the plurality of interconnected conformable garment components so as to form a plurality of separate garment components each having at least one discrete elasticized area contiguous with the unheated zones of the elastic material affixed thereto.

12. The combination set forth in claim 11 wherein said heat treating means is adapted to subject said selected spaced zones to temperatures in the range of 175° F. to 225° F.

13. Apparatus for forming a conformable garment having one or more discrete elasticized areas comprising, in combination: means for stretching at least one ribbon of thermoplastic elastomeric material; means for immobilizing the stretched material in its extended state; means for bonding the immobilized stretched ribbon to a continuous moving web suitable for use in forming a plurality of interconnected, but severable, like conformable garments having at least one selected discrete elasticized area on a high speed production basis; and means for heating spaced discrete areas of the immobilized stretched material so as to "kill" the elastic properties thereof in the spaced heated areas while leaving the elastic properties of the intermediate unheated areas thereof unaltered so that upon severing the web a plurality of like conformable garments are formed each having at least one discrete elasticized area contiguous with the unheated areas of the elastic ribbon bonded thereto.

14. In a method of elasticizing selected separated discrete areas of a garment or the like wherein a thermoplastic elastomeric material is employed to impart elasticity thereto and including the steps of:
 (a) stretching a thermoplastic elastomeric material;
 (b) immobilizing the stretched material in its extended state;
 (c) transferring the material while maintaining the material in its stretched immobilized condition;
 (d) applying adhesive to at least a portion of the stretched immobilized material;
 (e) adhesively bonding the material to a continuous web defining a plurality of interconnected garments and moving at a relatively high speed while maintaining the material in its stretched immobilized state relative to the web; and,
 (f) severing the web intermediate adjacent ones of the plurality of interconnected garments,
 the improvement comprising heating selected spaced discrete areas of the material while maintaining the material in its stretched immobilized condition so as to kill the elastic properties of the material in the spaced heated areas while leaving the elastic properties in the intervening unheated areas thereof unaltered so that upon severing of the web intermediate adjacent ones of the plurality of interconnected garments the unheated intervening areas of the material bonded to the web are permitted to contract and thereby elasticize the contiguous portions of the garment to which the material is bonded.

15. The method as set forth in claim 14 further characterized in that said garment is a disposable diaper.

16. The method as set forth in claim 15 further characterized in that the continuous web is suitable for use as one of a diaper facing sheet or a diaper backing sheet and wherein said stretched immobilized thermoplastic material is adhesively bonded adjacent the longitudinal opposed edges of said continuous web and is heat treated so that upon severing said web into a series of diapers the non-heated areas of the thermoplastic elastomeric material contract and thereby elasticize the crotch sections of one of the diaper sheets.

17. The method as set forth in claim 16 wherein the diaper sheets are fluid impermeable diaper backing sheets.

18. The method as set forth in claim 16 wherein the diaper sheets are fluid impermeable diaper sheets formed of polyethylene.

19. The method as set forth in claim 16 wherein the thermoplastic elastomeric material is a urethane.

20. The method as set forth in claim 18 wherein the thermoplastic elastomeric material is a urethane.

21. The method of elasticizing selected spaced discrete areas of a garment or the like comprising the steps of:
  (a) feeding a ribbon of thermoplastic elastomeric material of the type which loses its elastic properties when subjected to heat towards a high friction surface;
  (b) stretching the ribbon of thermoplastic elastomeric material;
  (c) frictionally engaging the ribbon of thermoplastic elastomeric material while in the stretched state with the high friction surface so as to immobilize the material relative to the surface;
  (d) heating selected spaced areas of the stretched immobilized ribbon of thermoplastic elastomeric material so as to kill the elastic properties thereof relative to the underlying high friction surface in the heated areas while leaving the elastic properties thereof in the unheated areas unaltered;
  (e) applying adhesive to at least portions of the stretched immobilized ribbon;
  (f) adhesively bonding the stretched ribbon to a continuous web defining a plurality of interconnected garments and moving at a relatively high speed while maintaining the ribbon in its stretched immobilized state relative to the web; and,
  (g) severing the web intermediate the plurality of interconnected garments so as to permit the unheated areas of the material to contract and thereby elasticize the continguous portions of the garments to which the material is bonded.

22. The method as set forth in claim 21 wherein adhesive is applied to the ribbon of thermoplastic elastomeric material as a continuous fine bead.

23. The method as set forth in claim 21 wherein the web is formed of polyethylene, the thermoplastic elastomeric material is a urethane, and the selected spaced areas of the urethane are subjected to heat in the range of 175° F. to 225° F.

24. The method as set forth in claim 23 wherein the garment is a diaper.

25. The method of elasticizing selected spaced discrete areas of a garment or the like comprising the steps of:
  (a) feeding a pair of ribbons of thermoplastic elastomeric material of the type which loses its elastic properties when subjected to heat towards a high friction surface;
  (b) stretching the ribbons of thermoplastic elastomeric material;
  (c) frictionally engaging the ribbons of thermoplastic elastomeric material while in the stretched state with the high friction surface so as to immobilize the material relative to the surface;
  (d) heating selected spaced areas of the stretched immobilized ribbons of thermoplastic elastomeric material so as to kill the elastic properties thereof relative to the underlying high friction surface in the heated areas while leaving the elastic properties thereof in the unheated areas unaltered;
  (e) applying adhesive to at least portions of the stretched immobilized ribbons;
  (f) adhesively bonding the stretched ribbons to a continuous web defining a plurality of interconnected garment components and moving at a relatively high speed while maintaining the ribbons in their stretched immobilized state relative to the web; and,
  (g) severing the web intermediate the plurality of interconnected garment components so as to permit the unheated areas of the material to contract and thereby elasticize the contiguous portions of the garment components to which the material is bonded.

26. The method as set forth in claim 25 wherein adhesive is applied to each of the ribbons of thermoplastic elastomeric material as a continuous fine bead.

27. The method as set forth in claim 25 wherein the web is formed of polyethylene, the thermoplastic elastomeric material is a urethane, and the selected spaced areas of the urethane are subjected to heat in the range of 175° F. to 225° F.

28. The method as set forth in claim 27 wherein the garment is a diaper.

29. Apparatus for forming an elasticized conformable garment on a high speed production basis comprising, in combination, a frame, means carried by said frame for conveying a continuous web comprising a plurality of interconnected garment components, spool means carried by said frame for holding n (where n equals any whole integer) spools of thermoplastic elastomeric material in continuous ribbon form, first drive means for unwinding the n ribbon(s) of elastomeric material from said n spool means, an adhesive applying means for applying adhesive to the n ribbon(s) of elastomeric material and second drive means for delivering the n ribbon(s) of elastomeric material into intimate face-to-face contact with the web, means for driving said first drive means, means for driving said second drive means at a velocity higher than the velocity of said first drive means so as to stretch the n ribbon(s) of elastomeric material, means for immobilizing the n stretched ribbon(s) of elastomeric material, and means for selectively heating spaced discrete areas of the n ribbon(s) of elastomeric material so as to kill the elastic properties thereof in the heated areas while leaving the elastic properties thereof in the non-heated areas unaltered so that upon severing the web transversely intermediate the plurality of interconnected garment components, the non-heated areas of the n ribbon(s) of elastomeric material are free to contract and thereby elasticize the contiguous areas of the garments to which the n ribbon(s) of elastomeric material is attached.

30. The combination as set forth in claim 29 wherein n equals two.

31. The combination as set forth in claim 30 wherein the conformable garment is a diaper, the thermoplastic elastomeric material is a urethane, the continuous web is polyethylene suitable for the impermeable backing sheet of a diaper, and said heating means is adapted to subject spaced discrete areas of the thermoplastic elastomeric material is temperatures in the range of 175° F. to 225° F.

32. The combination as set forth in claim 31 wherein the opposed longitudinal edges of each diaper backing sheet are curved in the crotch defining portion thereof, and said heating means are shaped to heat spaced discrete areas of the two ribbons of thermoplastic elastomeric material while leaving curved unheated intermediate portions suitable for attachment to the curved intermediate crotch defining portions of the diaper backing sheets so that upon severing the web to form separate diaper components, the curved unheated portions of the two ribbons contract to elasticize the curved edges of the crotch section of each diaper component.

* * * * *